US012566492B2

(12) United States Patent
Abou Shousha

(10) Patent No.: US 12,566,492 B2
(45) Date of Patent: Mar. 3, 2026

(54) OCULAR ANOMALY DETECTION VIA CONCURRENT PRESENTATION OF STIMULI TO BOTH EYES

(71) Applicant: Heru Inc., Miami, FL (US)

(72) Inventor: Mohamed Abou Shousha, Fort Lauderdale, FL (US)

(73) Assignee: Heru Inc., Miami, FL (US)

( * ) Notice: Subject to any disclaimer, the term of this patent is extended or adjusted under 35 U.S.C. 154(b) by 770 days.

(21) Appl. No.: 17/816,635

(22) Filed: Aug. 1, 2022

(65) Prior Publication Data

US 2024/0036641 A1    Feb. 1, 2024

(51) Int. Cl.
*G06F 3/01* (2006.01)
*A61B 3/02* (2006.01)
*G02B 27/01* (2006.01)

(52) U.S. Cl.
CPC .............. *G06F 3/013* (2013.01); *A61B 3/022* (2013.01); *G02B 27/0172* (2013.01); *G02B 2027/0178* (2013.01)

(58) Field of Classification Search
CPC ........ G02B 27/0172; G02B 2027/0178; G06F 3/013
USPC ........................................................ 351/210
See application file for complete search history.

(56) References Cited

U.S. PATENT DOCUMENTS

| | | | | |
|---|---|---|---|---|
| 10,264,962 | B2 * | 4/2019 | Rotenstreich | ............ A61B 3/14 |
| 2014/0168383 | A1 * | 6/2014 | Murakami | ........... H04N 13/296 348/47 |

| | | | | |
|---|---|---|---|---|
| 2017/0365101 | A1 * | 12/2017 | Samec | .................. G16H 20/70 |
| 2019/0094552 | A1 | 3/2019 | Shousha | |
| 2019/0142270 | A1 | 5/2019 | Monhart et al. | |
| 2020/0008667 | A1 * | 1/2020 | Raviv | .................. A61B 3/0033 |
| 2021/0112226 | A1 * | 4/2021 | Abou Shousha | .... G02B 27/017 |
| 2021/0275013 | A1 * | 9/2021 | Alvarez | ............... G02B 27/017 |

(Continued)

FOREIGN PATENT DOCUMENTS

| | | | |
|---|---|---|---|
| WO | 2016179185 | A1 | 11/2016 |
| WO | 2018163166 | A2 | 9/2018 |
| WO | WO-2018203297 | A1 * | 11/2018 |

OTHER PUBLICATIONS

International Search Report and Written Opinion issued in corresponding International Application No. PCT/US2023/071405 on Nov. 13, 2023 (12 pages).

*Primary Examiner* — Pinping Sun
*Assistant Examiner* — Andrew R Wright
(74) *Attorney, Agent, or Firm* — Foley & Lardner LLP

(57)          ABSTRACT

In some embodiments, a wearable device performs a visual test that includes simultaneously presenting a first eye stimulus for a first eye of a user of the device and a second eye stimulus for a second eye of the user, where the first eye stimulus has a display characteristic level greater than a display characteristic level of the second eye stimulus. The display characteristic level of the first eye stimulus and second eye stimulus are sequentially increased until feedback information indicates detection of at least one of the first eye stimulus or the second eye stimulus by the user. In response to the feedback information indicating such detection by the user, the other stimulus is presented at one or more sequentially increasing display characteristic levels until the feedback information indicates detection of the other stimulus. Ocular anomaly information of the user is generated based on the feedback information.

20 Claims, 9 Drawing Sheets

(56) References Cited

U.S. PATENT DOCUMENTS

| 2023/0404385 A1* | 12/2023 | Kurz | A61B 3/063 |
| 2024/0277222 A1* | 8/2024 | Spiegel | A61B 5/1116 |

* cited by examiner

204a 242          241

204a 243          244          246          245

241          242

302

304a

304b 308a                    306                    308b

Right Eye                    Left Eye 402b            404b        402a            404a Right Eye                          Left Eye 402b                404b    402a                404a

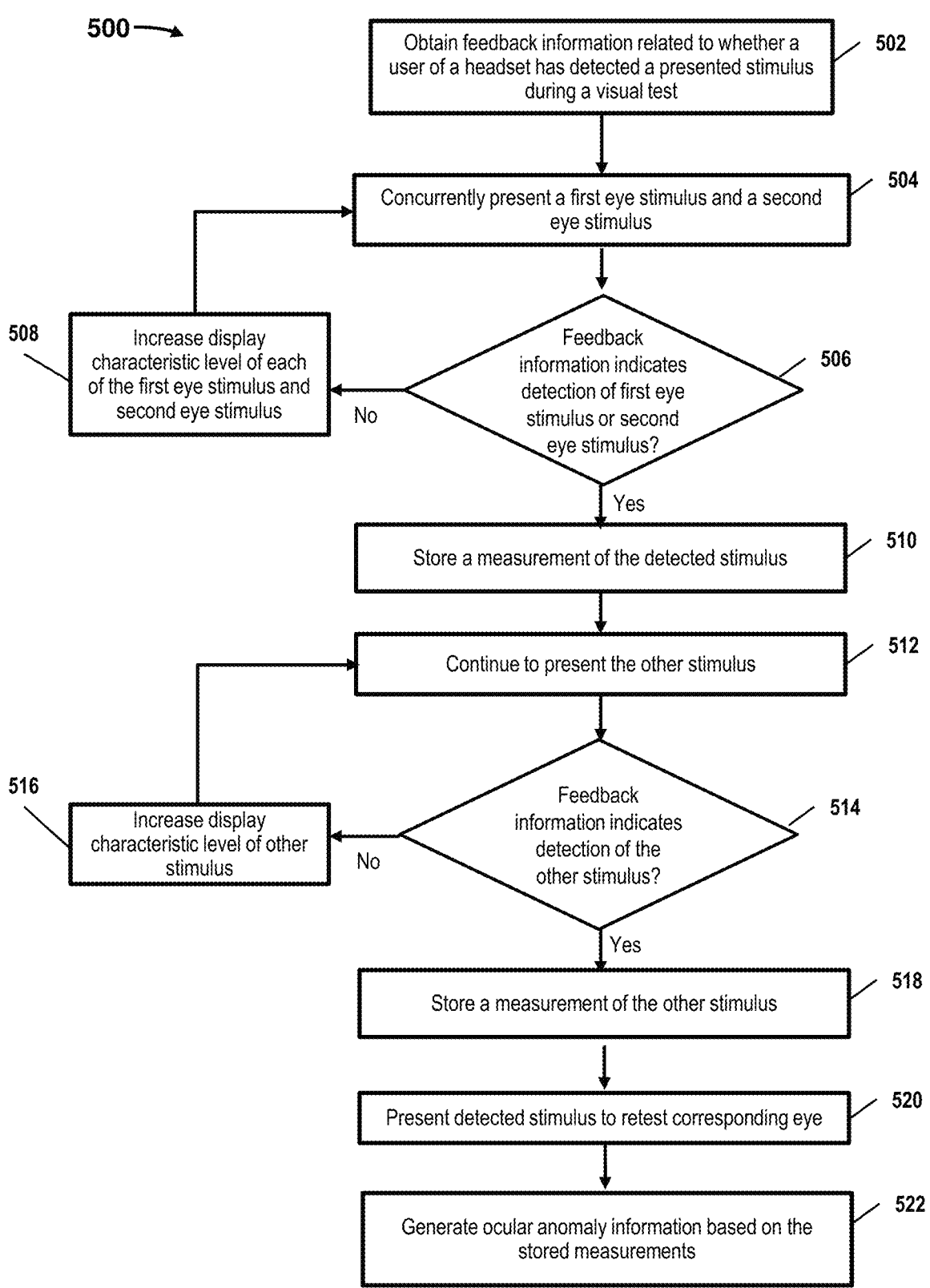

500 ➞

Obtain feedback information related to whether a user of a headset has detected a presented stimulus during a visual test — 502

Concurrently present a first eye stimulus and a second eye stimulus — 504

508 — Increase display characteristic level of each of the first eye stimulus and second eye stimulus 506 — Feedback information indicates detection of first eye stimulus or second eye stimulus?

No

Yes

Store a measurement of the detected stimulus — 510

Continue to present the other stimulus — 512

516 — Increase display characteristic level of other stimulus

514 — Feedback information indicates detection of the other stimulus?

No

Yes

Store a measurement of the other stimulus — 518

Present detected stimulus to retest corresponding eye — 520

Generate ocular anomaly information based on the stored measurements — 522

FIG. 5

OCULAR ANOMALY DETECTION VIA CONCURRENT PRESENTATION OF STIMULI TO BOTH EYES

BACKGROUND

A wearable device can be used to perform vision testing to determine vision defects and eye-related conditions by testing an eye's sensitivity to visual stimuli. For example, the wearable device presents a visual stimulus on a portion of its display and determines whether a user wearing the wearable device has observed the visual stimulus. Each eye is tested to measure the different sensitivities of each eye to visual stimuli. Because a movement of one eye will generally cause the other eye to also move, visual test stimuli are typically presented to one eye at a time during a visual test to avoid inaccurate test results impacted by reactions of the other eye.

SUMMARY

Aspects of the invention relate to methods, apparatuses, or systems for facilitating ocular anomaly detection. As an example, by presenting stimuli simultaneously to the eyes of a user at differing contrast levels (or other differing characteristics) and receiving feedback information from a user indicating a detection of such stimuli, a system may determine ocular anomalies associated with a user's eye, with reduced testing time while maintaining test accuracy.

While conventional systems may exist to detect ocular anomalies, these conventional systems are typically slow, waste valuable computer processing resources, and only present stimuli to an eye of a user one at a time when testing for individual conditions specific to each eye. For example, such conventional systems may only test one eye at a time. As such, for each eye of the user, the test may need to be repeated using the same or similar steps, which may not only waste computer processing resources, but can also result in long testing times and, thus, poor user experience. As discussed above, especially when testing for individual conditions specific to each eye, conventional systems generally only present visual test stimuli to one eye at a time during a visual test to avoid inaccurate test results impacted by reactions of the other eye (e.g., because a movement of one eye will cause the other eye to also move).

To solve one or more of the foregoing technical problems, for example, a wearable device may present a stimulus to each eye of the user simultaneously at differing contrast levels while sequentially increasing the contrast levels to generate ocular anomaly information based on feedback information.

In some embodiments, a stimulus may be presented to a first eye of the user and a second eye of the user, simultaneously, where the first eye stimulus has a higher contrast level than the contrast level of the second eye stimulus. The contrast levels of each of the first eye stimulus and the second eye stimulus may sequentially increase until feedback information indicates detection of at least one of the first eye stimulus or the second eye stimulus by the user. In response to the feedback information indicating detection of the first eye stimulus or the second eye stimulus, the other eye stimulus (e.g., the eye stimulus that has not been detected by the user) may be sequentially increased until the feedback information indicates detection of the other eye stimulus. Based on the feedback information, ocular anomaly information may be generated.

Various other aspects, features, and advantages of the invention will be apparent through the detailed description of the invention and the drawings attached hereto. It is also to be understood that both the foregoing general description and the following detailed description are examples, and not restrictive of the scope of the invention. As used in the specification and in the claims, the singular forms of "a," "an," and "the" include plural referents unless the context clearly dictates otherwise. In addition, as used in the specification and in the claims, the term "or" means "and/or" unless the context clearly dictates otherwise. Additionally, as used in the specification, "a portion" refers to a part of, or the entirety of (i.e., the entire portion), a given item (e.g., data) unless the context clearly dictates otherwise. Furthermore, a "set" may refer to a singular form or a plural form, such as that a "set of items" may refer to one item or a plurality of items.

BRIEF DESCRIPTION OF THE DRAWINGS

FIG. 5 is a flowchart illustrating a process for concurrent visual tests, in accordance with one or more embodiments.

DETAILED DESCRIPTION

In the following description, for the purpose of explanation, numerous specific details are set forth in order to provide a thorough understanding of the embodiments of the invention. It will be appreciated, however, by those having skill in the art that the embodiments of the invention may be practiced without these specific details or with an equivalent arrangement. In other cases, well-known structures and devices are shown in block diagram form in order to avoid unnecessarily obscuring the embodiments of the invention.

Figure 1:
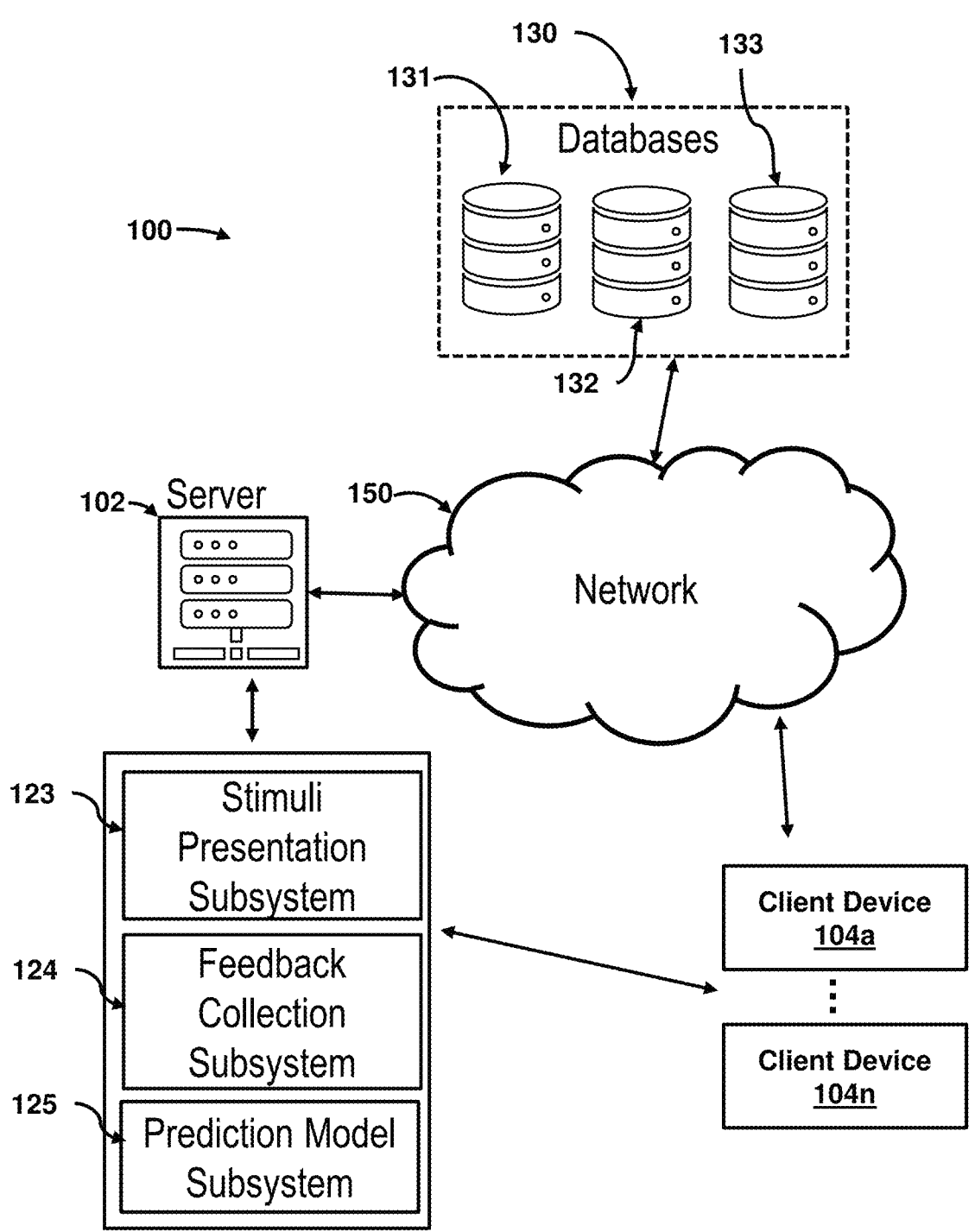
FIG. 1 illustrates a system for facilitating vision testing and collecting feedback information, in accordance with one or more embodiments.

FIG. 1 shows a system 100 for facilitating vision testing and collecting feedback information, in accordance with one or more embodiments. As shown in FIG. 1, system 100 may include server(s) 102, client device 104 (or client devices 104a-104n), or other components. Server 102 may include stimuli presentation subsystem 123, feedback collection subsystem 124, prediction model subsystem 125, or other components. In some embodiments, although not shown, client device 104 may also include stimuli presentation subsystem 123, feedback collection subsystem 124, prediction model subsystem 125, or other components. Each client device 104 may include any type of mobile terminal, fixed terminal, or other device. By way of example, client device 104 may include a user device, a desktop computer, a notebook computer, a tablet computer, a smartphone, a wearable device, or other client device. Users may, for instance, utilize one or more client devices 104 to interact with one another, one or more servers, or other components of system 100. As used herein, "client device," "user device," and "mobile device" may refer to the same device unless the context in which such terms are used dictates otherwise.

It should be noted that, while one or more operations are described herein as being performed by particular components of client device 104, those operations may, in some embodiments, be performed by other components of client device 104 or other components of system 100. As an example, while one or more operations are described herein as being performed by components of client device 104, those operations may, in some embodiments, be performed by components of server 102. It should also be noted that, while one or more operations are described herein as being performed by particular components of server 102, those operations may, in some embodiments, be performed by other components of server 102 or other components of system 100. As an example, while one or more operations are described herein as being performed by components of server 102, those operations may, in some embodiments, be performed by components of client device 104. It should further be noted that, although some embodiments are described herein with respect to machine learning models, other prediction models (e.g., statistical models or other analytics models) may be used in lieu of or in addition to machine learning models in other embodiments (e.g., a statistical model replacing a machine learning model and a non-statistical model replacing a non-machine-learning model in one or more embodiments).

In some embodiments, system 100 may perform visual tests for ocular anomaly detection for a user by concurrently testing the user's left eye and right eye. For example, during a visual test, the vision system simultaneously presents a corresponding visual stimulus to each eye and measures feedback information to determine whether either eye detected the corresponding stimulus. One of the stimuli is displayed with a greater display characteristic level than the stimulus presented to the other eye, where the display characteristic level includes, for example, a brightness level, a contrast level, a sharpness level, or an opacity level. In some embodiments, a greater display characteristic level may be associated with a lower value. For example, in the case that a brightness level is measured in decibels (dB), a lower value such as 5 dB may appear visually brighter to the user as opposed to 10 dB. If the feedback information indicates that neither stimulus has been detected, the vision system sequentially increases the display characteristic level of the stimuli (e.g., until at least one of the stimuli is detected or other criteria is satisfied). The display characteristic levels of the stimuli can be increased in parallel at each step. For example, a first eye stimulus may be displayed in each step with a greater display characteristic level than a second eye stimulus. As another example, a first eye stimulus and a second eye stimulus may be displayed in each step with a greater display characteristic level. In response to at least one of the stimuli being detected, the other, non-detected stimulus can then be presented at sequentially increasing display characteristic levels (e.g., until it is detected or other criteria is satisfied). The vision system generates ocular anomaly information for the user based on the display characteristic levels at which each eye detected the corresponding stimulus.

Performing individual visual testing of both of a user's eyes requires time and resources, but by concurrently testing both eyes via one or more techniques described herein, the vision system performs a visual test faster than if each eye is tested individually. Thus, various implementations of the visual testing techniques described herein may reduce the time and resources expended to perform such visual tests.

In some embodiments, the user device 104 sends and receives messages through the network 150 to communicate with a server 102, where the server 102 may include one or more non-transitory storage media storing program instructions to perform one or more operations such as generating instructions for visual tests, training machine learning models, storing or processing ocular anomaly information, or other operations. It should further be noted that, while one or more operations are described herein as being performed by particular components of the system 100, those operations may be performed by other components of the system 100 in some embodiments. For example, operations described in this disclosure as being performed by the server 102 may instead be performed by the user device 104, where program code or data stored on the server 102 may be stored on the user device 104 or another client computer device instead. Similarly, in some embodiments, the server 102 may store program code or perform operations described as being performed by the user device 104. For example, the server may perform operations described as being performed by the stimuli presentation subsystem 123, the feedback collection subsystem 124, or the prediction model subsystem 125. Furthermore, although some embodiments are described herein with respect to machine learning models, other prediction models (e.g., a statistical model) may be used instead of or in addition to machine learning models. For example, a statistical model may be used to replace a neural network model in one or more embodiments to determine an ocular anomaly.

Figure 2A:
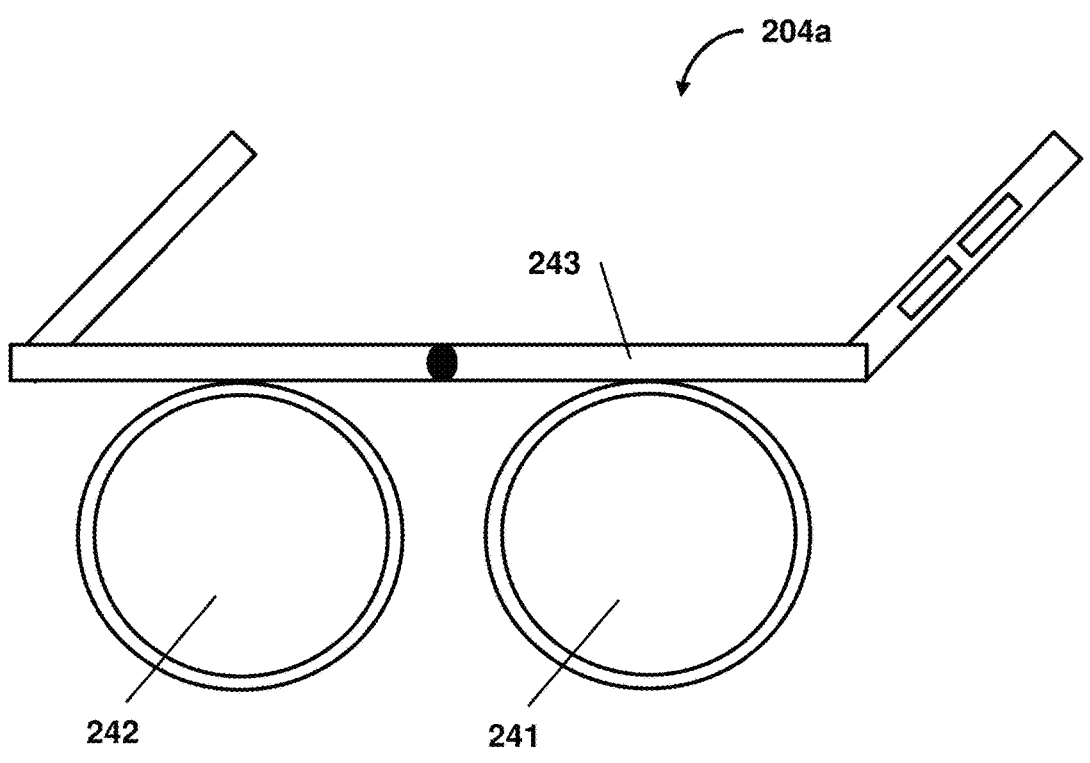
FIGS. 2A-2D show example user devices used for one or more vision tests, in accordance with one or more embodiments.
Figure 2B:
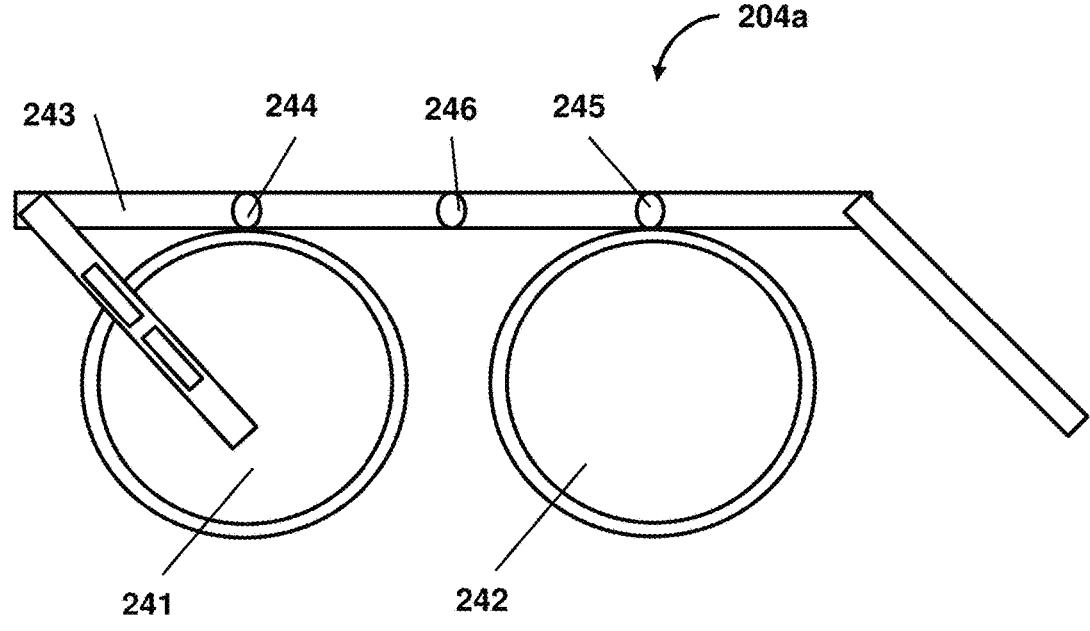

System 100 presents visual stimuli (e.g., shapes, text, or images) on a display of the user device 104. As an example, referring to FIGS. 2A and 2B, where the user device is a wearable device (e.g., a headset), wearable device 204a may include a housing 243, a left eye display 241, and a right eye display 242. The left eye display 241 and right eye display 242 can be positioned with respect to the housing 243 to fit an orbital area on a user such that the left eye display 241 is positioned substantially in front of a left eye of a user when the wearable device 204a is worn and the right eye display 242 is positioned in front of a right eye of the user. Each of the displays 241-242 is configured to present respective visual stimuli or other images to the user during a visual test.

The wearable device 204a further includes one or more eye tracking sensors, such as a left eye sensor 244 and a right eye sensor 245. Other embodiments of the wearable device 204a can include a single eye tracking sensor (e.g., single eye tracking sensor 246) or more than two eye tracking sensors. The sensor or sensors can be directionally aligned to point towards a presumed pupil region of a user for line-of-sight tracking or pupil tracking. During a visual test, signals output by the eye tracking sensors can be processed by the system 100 to detect feedback information, including responses of a user's eyes to a stimulus or stimuli presented on the displays of the wearable device. Example eye tracking sensors include visual spectrum cameras, infrared cameras, photodetectors, or infrared sensors. For example, the eye tracking sensors may include cameras configured to track pupil movement and determine and track visual axes of the user.

Figure 2C:
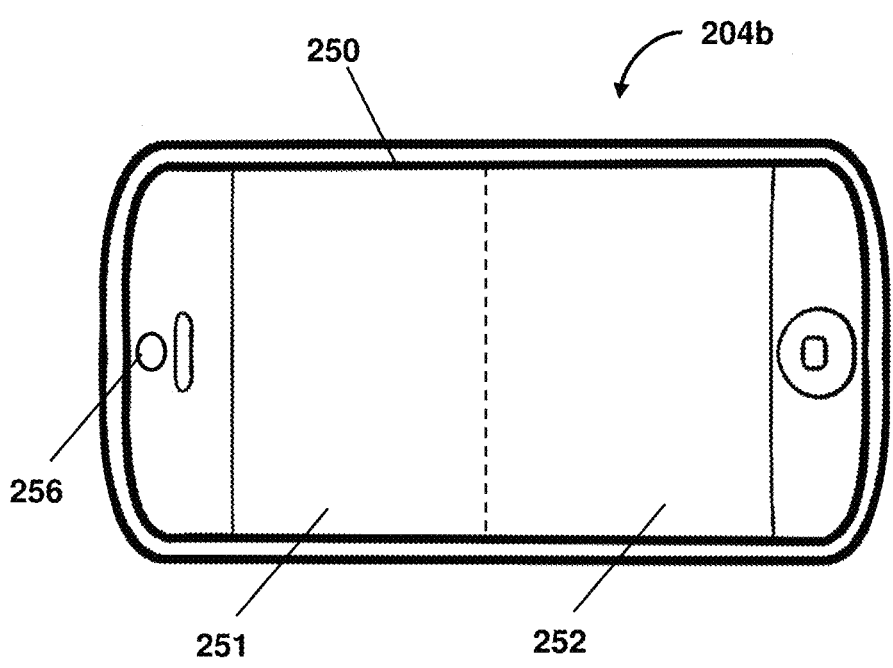

As another example, referring to FIG. 2C, where the user device is a mobile device 204b (e.g., a head-mounted display or other wearable device, tablet, or other mobile device), the mobile device may include a display that is partitioned into two portions. That is, while the mobile device includes a display 250, the display may be partitioned (e.g., via software or hardware) into first display portion 251 and second display portion 252 that may correspond to a right eye display and a left eye display, respectively. Additionally, the mobile device may also include one or more eye tracking sensors, such as eye tracking sensor 256. As such, the systems and methods described herein are not merely limited to wearable devices, but may also be performed on one or more non-wearable devices.

Figure 2D:
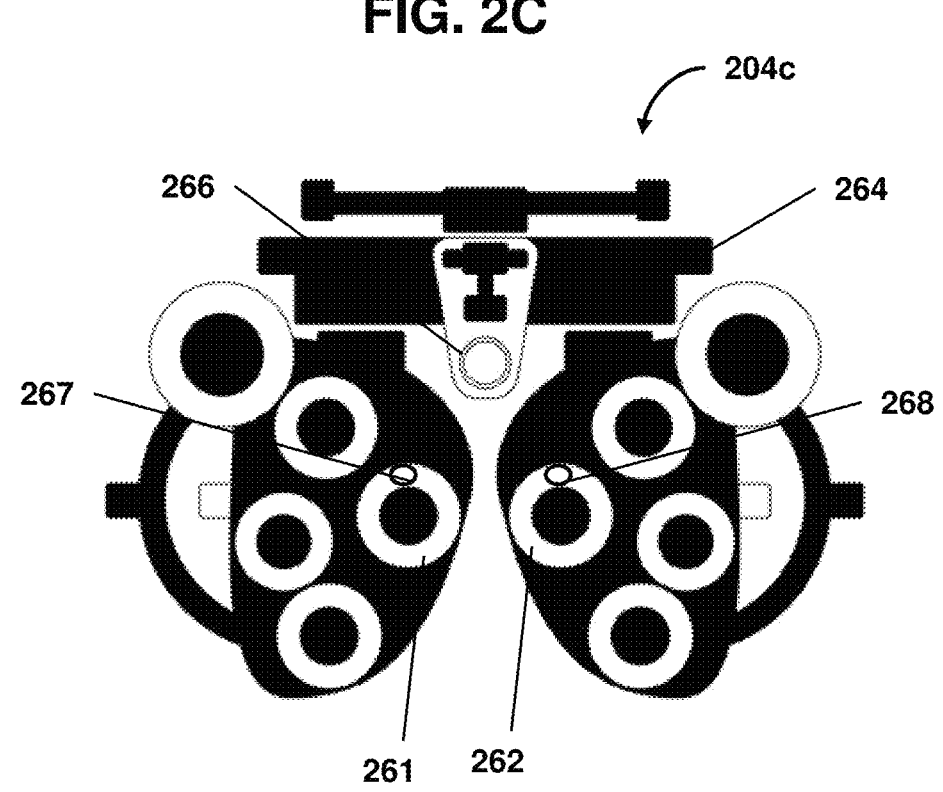

As yet another example, referring to FIG. 2D, where the user device is eye exam equipment such as a refractor 204c, the refractor may include a housing 264, a left eye display 261, and a right eye display 262. The left eye display 261 and right eye display 262 can be positioned with respect to the housing 264 to fit an orbital area on a user such that the left eye display 261 is positioned substantially in front of a left eye of a user when the refractor 204c is used and the right eye display 262 is positioned in front of a right eye of the user. Each of the displays 261-262 is configured to present respective visual stimuli or other images to the user during a visual test. The refractor 204c further includes one or more eye tracking sensors, such as a left eye sensor 267 and a right eye sensor 268. Other embodiments of the refractor 204c can include a single eye tracking sensor (e.g., single eye tracking sensor 266) or more than two eye tracking sensors.

During or after a visual testing operation, the system 100 obtains feedback information related to the displayed stimuli, where the feedback information may indicate whether or how an eye responds to one or more stimuli. For example, some embodiments may use the wearable device 104 to collect feedback information that includes various eye-related characteristics. In some embodiments, the feedback information may include an indication of a response of an eye to the presentation of a dynamic stimulus at a given display location (e.g., a location at which a stimulus is presented). Alternatively, or in addition, the feedback information may include an indication of a lack of a response to such a stimulus. The response or lack of response may be determined based on one or more eye-related characteristics, such as an eye movement, a gaze direction, a distance in which an eye's gaze traveled in the gaze direction, a pupil size change, a user-specific input, etc. In some embodiments, the feedback information may include image data or results based on image data. For example, some embodiments may obtain an image or sequence of images (e.g., in the form of a video) of an eye captured during a testing operation as the eye responds to a stimulus. The image of the eye may be an image of a retina of the eye, such as an image of the overall retina or a portion thereof, an image of a cornea of the eye, such as an image of the overall cornea or a portion thereof, or another eye image.

The system 100 can detect one or more ocular anomalies of an eye and update associated ocular anomaly information based on feedback information indicating eye responses to stimuli. Ocular anomalies detected by the system 100 may, for example, relate to a visual field defect, a dark adaptation defect, eye misalignment, or anomalies in pupil movement or size. For example, some embodiments may use a prediction model to detect a non-responsive region of a visual field or another ocular anomaly of a visual field portion associated with the ocular anomaly. In some embodiments, a region associated with an ocular anomaly may be determined by a selection of locations or regions of an eye's visual field that fail to satisfy one or more vision criteria. In some embodiments, satisfying a set of vision criteria for a visual field location may include determining whether an eye responded to a stimulus presented at the display location mapped to the visual field location, where different presented stimuli may vary in brightness, contrast, color, shape, size, or transparency.

In some embodiments, data used or updated by one or more operations described in this disclosure may be stored in a set of databases 130. In some embodiments, the server 102, the user device 104, or other computer devices associated with the system 100 may access the set of databases to perform one or more operations described in this disclosure. For example, a prediction model used to determine ocular anomaly information may be obtained from a first database 131, where the first database 131 may be used to store prediction models or parameters of prediction models. Alternatively, or in addition, the set of databases 130 may store feedback information collected by the wearable device 104 or results determined from the feedback information. For example, a second database 132 may be used to store a set of user profiles that include or link to feedback information corresponding with eye measurement data for the users identified by the set of user profiles. Alternatively, or in addition, the set of databases 130 may store instructions indicating different types of testing procedures. For example, a third database 133 may store a set of testing instructions that causes stimuli to be presented at certain locations on the wearable device 104, with certain display characteristic levels, in order to test for different types of ocular anomalies.

According to implementations herein, the system 100 performs a visual test of a user by concurrently displaying stimuli to both eyes of a user. During a test, a stimulus is presented concurrently to each eye, where the stimulus presented to one eye is displayed with a greater display characteristic level than the stimulus presented to the other eye. If neither stimulus is detected, the system sequentially increases the display characteristic level of the stimuli until one is detected. The other, non-detected stimulus can then be presented at sequentially increasing display characteristic levels until it is detected. By concurrently testing both eyes, the system 100 performs a visual test faster than if each eye is tested individually.

Subsystems 123-125

A visual test can be performed based on operations by the stimuli presentation subsystem 123, the feedback collection subsystem 124, and the prediction model subsystem 125. For example, a user device may receive data from server 102 over network 150 to perform a visual test on a user. In some embodiments, the user device may be a desktop computer, a notebook computer, a tablet computer, a smartphone, a wearable device, an ocular exam device, or other user device. As such, the user device may communicate with server 102 to provide feedback information to one or more subsystems of subsystems 123, 124, and 125.

In some embodiments, stimuli presentation subsystem 123 presents a set of stimuli on a user device. For example, stimuli presentation subsystem 123 may present a set of stimuli on a user interface of a user device. For instance, where the user device is a laptop computer, stimuli presentation subsystem 123 may present a set of stimuli on the display of the laptop computer. Likewise, where the user device is a mobile device, stimuli presentation subsystem 123 may present a set of stimuli on the display of the mobile device. As another example, where the user device is a wearable device, stimuli presentation subsystem 123 may present a set of stimuli on the lenses/displays of the wearable device. As yet another example, where the user device is ophthalmology equipment (or other eye exam equipment) such as a refractor, stimuli presentation subsystem 123 may present the set of stimuli on one or more lenses of the refractor. The set of stimuli may be presented in locations according to one or more instructions. For example, a test of visual characteristics of a peripheral region of a user's vision includes instructions that cause the stimuli presentation subsystem 123 to display stimuli at locations, respective of the user device display, that correspond to the peripheral region of the user's field of vision. A test of visual characteristics of a foveal region includes instructions that cause the stimuli presentation subsystem 123 to display the stimuli at locations, respective of the user device display, that correspond to the foveal region of the user's field of vision.

Figure 3A:
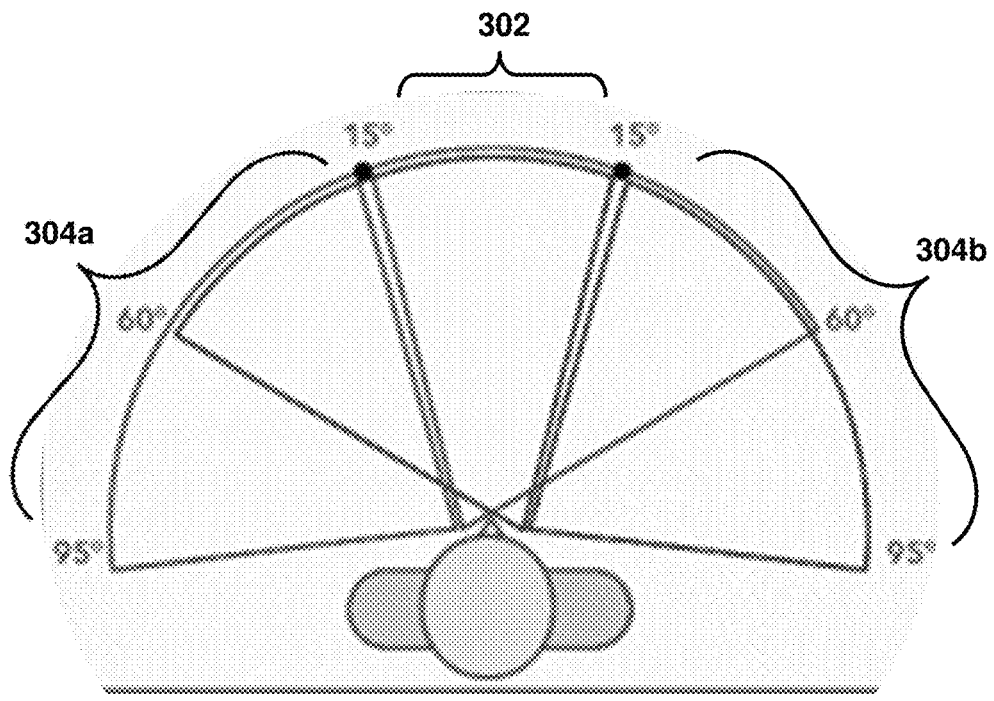
FIGS. 3A-3B illustrate a user's field of vision, in accordance with one or more embodiments.
Figure 3B:
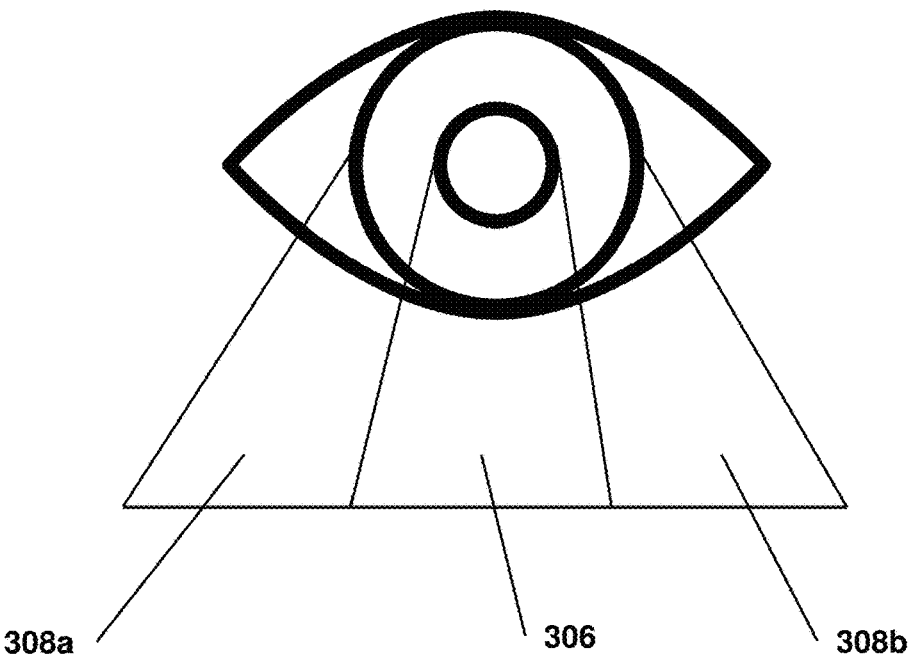

To clarify, referring to FIG. 3A, a user's field of vision may represent an area of space that the user can see. The user's field of vision may include one or more angular segments. Each angular segment may be associated with at least a portion of the user's field of vision. For example, first angular portion 302 may correspond to the foveal vision of a user's field of vision and second angular portion 304a and third angular portion 304b may correspond to the peripheral vision of a user's field of vision. It should be noted, that such examples are exemplary and the one or more of the first angular portion 302, second angular portion 304a and third angular portion 304b may overlap by a threshold degree, or in some cases may not overlap. As FIG. 3A shows a user's field of vision when the user has both eyes open (e.g., can see with both eyes and does not have a missing eye or other visual defect), FIG. 3B shows a diagram of one eye of a user and corresponding foveal and peripheral vision portions. For example, first portion 306 may correspond to the foveal vision of the user's field of vision for an eye of the user. Second portion 308a may correspond to a peripheral vision portion of the user's field of vision for the eye of the user. Similarly, third portion 308b may correspond to another peripheral vision portion of the user's field of vision for the eye of the user. In some embodiments, the peripheral vision portions of an eye of a user may include the foveal vision portions whereas in other embodiments, the peripheral vision portions of an eye of a user may be distinct from that of the foveal vision portions of the user.

Figure 4A:
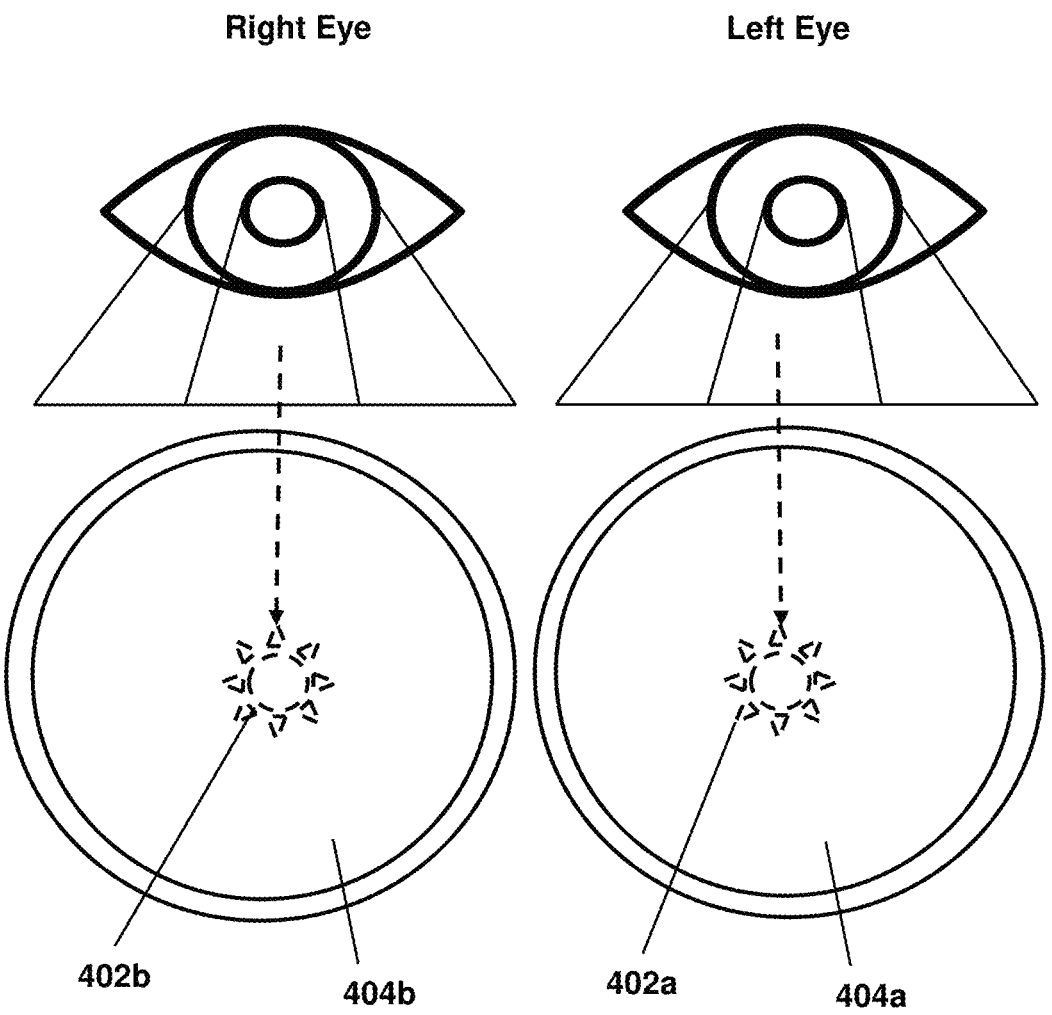
FIGS. 4A-4B illustrate presenting stimuli at one or more locations associated with one or more portions of a user's visual field, in accordance with one or more embodiments.
Figure 4B:
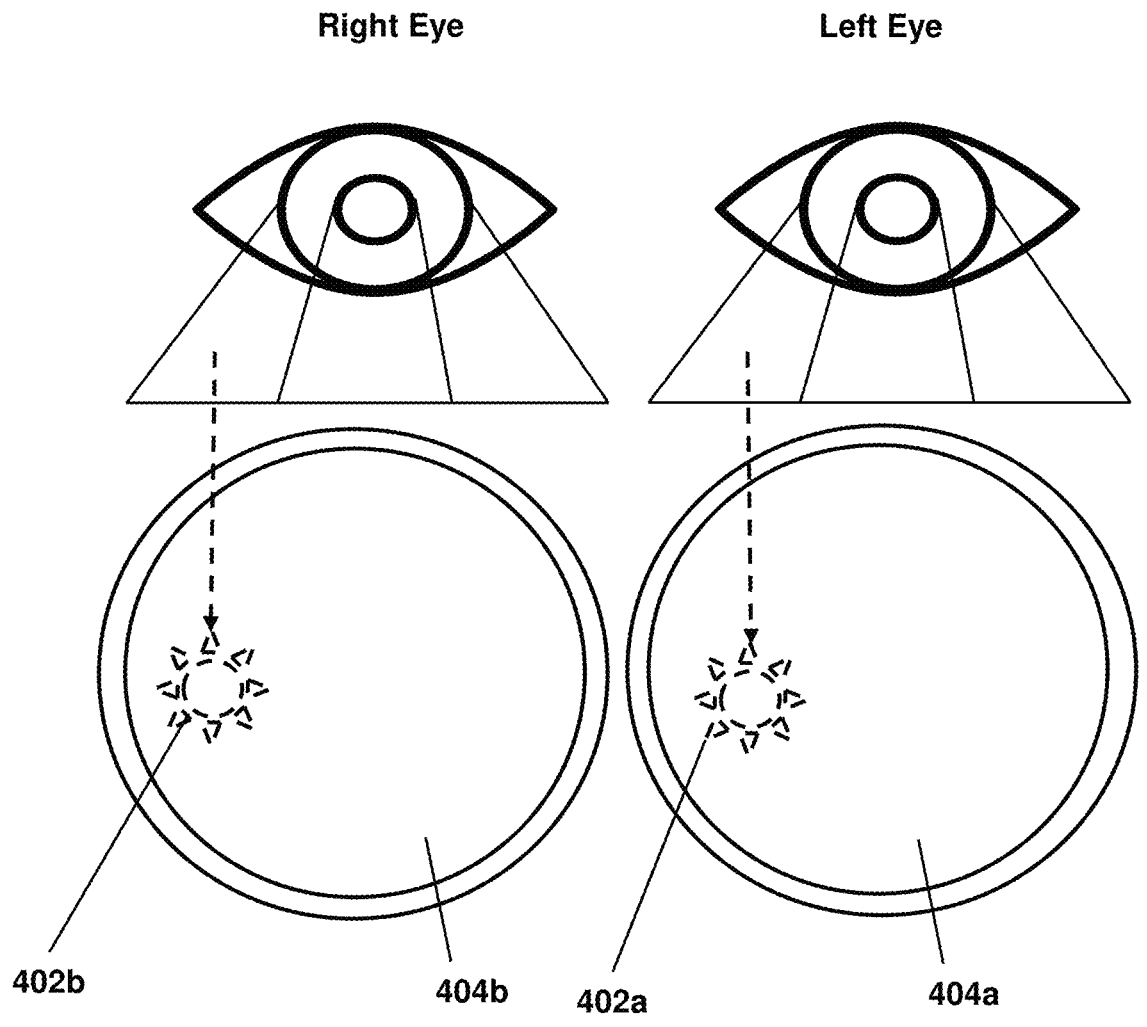

As an example, referring to FIG. 4A, where the user device is a wearable device, stimuli presentation subsystem 123 presents a set of stimuli on the wearable device. A left eye stimulus 402a is presented via the left eye display 404a and a right eye stimulus 402b is presented via the right eye display 404b. The location of the stimuli on the respective displays and display characteristic levels of the respective stimuli can be specified according to instructions for the type of visual test that is being implemented by the system 100. As an example, as shown in FIG. 4A, a test of visual characteristics of a foveal region of a user's vision includes instructions that cause the stimuli presentation subsystem 123 to display left and right eye stimuli at locations on the displays 404 that correspond to foveal region of the user's field of vision. As another example as shown in FIG. 4B, a test of visual characteristics of a peripheral region of a user's vision includes instructions that cause the stimuli presentation subsystem 123 to display the left and right eye stimuli at locations on the displays 404 that correspond to the peripheral region of the user's field of vision. Some types of visual tests can further include instructions that cause the stimuli presentation subsystem 123 to present stimuli that are additional to those described in the testing procedures discussed herein. For example, to test the ability of a user's eyes to adapt to darkness, the stimuli presentation subsystem

123 first bleaches the field of view with bright light before presenting a visual stimulus against a dark background.

In some embodiments, stimuli presentation subsystem 123 may determine the display location for a stimulus by first determining the location or region of a visual field of the user of the user device, such as wearable device. After determining the location or region of the visual field, some embodiments may then use a field-to-display map to determine which display location of the left eye display 404a and the right eye display 404b to use when displaying respective stimuli during a visual test. For example, some embodiments may determine that a previous sequence of sensor measurements indicated that a first region of a visual field has not yet been tested and select this first region for testing. Furthermore, a visual field location of a stimulus may include the field location mapped to or otherwise associated with the display location of the stimulus, where the mapping or association between the display and the field location is determined by a field-to-display map.

The feedback collection subsystem 124 processes signals obtained from eye tracking sensors to record feedback information indicating eye responses to the set of stimuli presented on the user device. The feedback collection subsystem 124 can use any combination of rules, statistical analyses, or trained machine learning models to predict whether a user detected a stimulus based on the signals obtained from the eye tracking sensors. In some implementations, the feedback collection subsystem 124 combines eye tracking data with explicit feedback from the user to predict detection of a stimulus or to update the prediction models.

The prediction model subsystem 125 retrieves feedback information from the feedback collection subsystem 124 and stimuli information, such as stimuli locations and display characteristic levels of the displayed stimuli, from the stimuli presentation subsystem 123. Based on the feedback information and the stimuli information, the prediction model subsystem 125 generates ocular anomaly information of a user. In some implementations, the prediction model subsystem 125 applies one or more rules or trained machine learning models to the feedback information and stimuli information, where the rules or models are configured to output information that indicates whether an ocular anomaly is present and/or the nature of such an ocular anomaly. The prediction model subsystem 125 can further provide stimuli information, feedback information, and output ocular anomaly information to a machine learning model to update the parameters of the machine learning model to predict ocular anomalies based on new inputs.

FIG. 5 is a flowchart illustrating a process 500 for concurrent ocular anomaly testing of both of a user's eyes, according to some implementations. The process shown in FIG. 5 can be performed by the system 100. Other implementations of the process 500 can include additional, fewer, or different steps, and the steps can be performed in different orders.

At block 502, the feedback collection subsystem 124 obtains feedback information during a visual test, for example using one or more eye tracking sensors that track eyes of a user of a user device 104. The feedback information relates to whether the user has detected a stimulus presented on a display of the user device during the course of the visual test.

At block 504, the stimuli presentation subsystem 123 concurrently presents a first eye stimulus via a first eye display (or a portion of a user device display that is within a possible field of view of the first eye) and a second eye stimulus via a second eye display (or a portion of a user device display that is within a possible field of view of the second eye). The first eye stimulus and second eye stimulus may be presented at similar corresponding locations of the first and second displays or at different locations. For example, in some types of tests, the first and second stimuli are both displayed within a region of the corresponding displays that correspond to a foveal region of a user's vision (e.g., as shown in FIG. 4A). The foveal region of the user's vision may correspond to a location on the first and second displays that may be substantially centered with respect to the first and second displays. For instance, as shown in FIG. 4A, right eye stimulus 402b and left eye stimulus 402a may be presented at locations that correspond to the foveal region of the user's vision (e.g., substantially centered with respect to the first and second displays, respectively). In other types of tests, the first and second stimuli are both displayed within a region of the corresponding displays that correspond to a peripheral region of a user's vision (e.g., as shown in FIG. 4B), such as above, below, to the left, or to the right of the foveal region. The peripheral region of a user's vision may correspond to a location on the first and second displays that may be substantially off-center with respect to the first and second displays. For instance, as shown in FIG. 4B, right eye stimulus 402b and left eye stimulus 402a may be presented at locations that correspond to the peripheral region of the user's vision (e.g., substantially off-center with respect to the first and second displays, respectively). In still other test types, one of the stimuli is presented in the foveal region while the other is presented in the peripheral region. Furthermore, each of the first and second eye stimuli can each represent a single stimulus (e.g., a single dot) or multiple stimuli (e.g., multiple dots displayed at different locations on the first eye display or the second eye display). Additionally, it should be noted that although FIGS. 4A and 4B indicate "right eye stimulus," "left eye stimulus," "right eye display," and "left eye display," such uses of the terms "right" and "left" are merely exemplary and that either one of "right" or "left" may be substituted for "first" or "second," in accordance with one or more embodiments.

When presenting the first eye stimulus and second eye stimulus in block 504, stimuli presentation subsystem 123 displays the first eye stimulus with a display characteristic level that is higher than a display characteristic level of the second eye stimulus. Example display characteristics levels that are adjustable by the system 100 include a contrast level (e.g., relative to a background of the user device displays), a brightness level, a sharpness level, or a transparency (or opacity) level.

Feedback collection subsystem 124 periodically determines, at block 506, whether the feedback information indicates the user has detected at least one of the stimuli. For example, if the user's eyes move towards one of the stimuli, the feedback collection subsystem 124 can determine that the user likely observed the stimulus. The system can perform processing on the data produced by the eye tracking sensors to distinguish between eye movements that are likely to indicate detection of a stimulus and eye movements that are unlikely to indicate detection. For example, feedback collection subsystem 124 may classify eye movements as indicating a stimulus detection if the user's eyes move at least a threshold amount or if they move and remain fixed near the location of one of the stimuli for at least a threshold amount of time. In other implementations, the feedback collection subsystem 124 determines that the feedback information indicates detection of a stimulus by applying a trained classifier that is configured to classify the feedback information as being indicative of stimulus detection or not being indicative of stimulus detection. In addition to or instead of using feedback from the eye tracking sensors, the system 100 can use explicit feedback from the user (e.g., a button press, a hand gesture, or a verbal utterance) to determine that the user observed at least one of the stimuli.

In one use case, where the user device is eye exam equipment, such as a refractor, the refractor may be configured to receive an input via one or more buttons. For instance, the one or more buttons may be configured to receive a user's explicit feedback (e.g., via a button press) indicating that the user observed at least one of the stimuli. As another example, where an ophthalmologist is physically looking at a users' eyes (e.g., during one or more vision tests), the ophthalmologist may determine that at least one eye of the user moves in association with one or more of the presented stimuli. As such, the ophthalmologist may provide feedback information using the one or more buttons or other input device to indicate that the user observed at least one of the stimuli.

If the feedback information does not indicate detection of the stimuli at block 506, the stimuli presentation subsystem 123 increases the display characteristic level of each stimuli at block 508 and returns to block 504, where the first eye stimulus and second eye stimulus are concurrently displayed with the increased display characteristic levels. In some implementations, the display characteristic levels of the first and second eye stimuli are increased in parallel, such that the display characteristic levels of the stimuli are increased by the same amount on a linear or logarithmic scale at block 508. For example, if the first eye stimulus was initially displayed at a brightness of 24 decibels (dB) and the second eye stimulus at 28 dB, the system increases the brightness levels of both stimuli by 2 dB to 22 dB and 26 dB, respectively. At each iteration of block 508 in this example, the stimuli presentation subsystem 123 can continue to increase each stimulus by 2 dB. Furthermore, the system 100 increases the display characteristic levels simultaneously in some implementations, while in other implementations increases the display characteristic levels at different times (e.g., by first increasing the display characteristic level of the second stimulus and subsequently increasing the display characteristic level of the first stimulus). In some embodiments, each stimulus is displayed continuously during the adjustment of its display characteristic level, such that the display characteristic level of the stimulus is increased without turning off the stimulus, for example. In other embodiments, one or both stimuli are turned off for a short time and redisplayed at the increased display characteristic level.

If the feedback information does indicate, at block 506, that the user detected at least one of the stimuli, the feedback collection subsystem 124 may store a measurement of the display characteristic level of one or both of the stimuli at block 510. For example, feedback collection subsystem 124 may store measurement of the display characteristic level of the one or both stimuli in second database 132. In some embodiments, the feedback collection subsystem 124 may store a measurement of the display characteristic level of the first eye stimulus, based on a prediction that the higher display characteristic level of the first eye stimulus means that it is more likely to have been detected than the second eye stimulus. In other implementations, the system 100 applies other rules or models to predict which stimulus was more likely to have been observed and stores the display characteristic level of the corresponding stimulus. For example, the system 100 determines that the first eye stimulus was likely detected if the user's eyes move towards the first eye stimulus, or that the second eye stimulus was likely detected if the user's eyes move towards the second eye stimulus. In another example, the system applies a model that is trained to predict the stimulus that was observed based on features such as the feedback information, locations of the stimuli relative to the user's eyes, an amount of time each stimulus was displayed, previous visual tests of the user, or other data.

Once the user has detected at least one of the stimuli, the stimuli presentation subsystem 123 continues to present, at block 512, the stimulus other than the one that was predicted to be detected. For example, if the first eye stimulus was predicted to be the detected stimulus given its higher display characteristic level, the system presents the second eye stimulus. If the second eye stimulus was predicted to be the detected stimulus (e.g., based on the user's eye movements), the system presents the first eye stimulus. Some implementations of the system cease presentation of the detected stimulus at block 512, presenting only the other stimulus until feedback information indicates the user has detected the other stimulus. Other implementations continue to display the detected stimulus at or below the display characteristic level at which the detected stimulus was observed (e.g., such that a user may not see the stimulus that is presented at or below the display characteristic level at which the detected stimulus was observed). In this way, the system may mitigate any inaccurate feedback information due to simultaneously presenting a stimuli which may have already been detected (e.g., the system may continue to test the other eye that has not yet detected a given stimulus without conflicting feedback information).

At block 514, the feedback collection subsystem 124 determines if the feedback information indicates the user has detected the other stimulus. The process of determining that the user has detected the stimulus can be similar to the process performed with respect to block 506. If the other stimulus has not been detected after a threshold amount of time, the stimuli presentation subsystem 123 increases the display characteristic level of the other stimulus at block 516 and returns to block 512, where the stimulus is displayed at the increased display characteristic level.

If the feedback information indicates detection of the other stimulus at block 514, the feedback collection subsystem 124 stores a measurement of the detected display characteristic level of the other stimulus at block 518.

In some embodiments, or after certain test results, the system 100 retests the eye corresponding to the stimulus that was determined to be detected first after the other stimulus has been detected at block 520. For example, if the system 100 predicted that the first eye stimulus was the stimulus detected at block 506 based on a presumption that the stimulus with the greater display characteristic level was more likely to be detected than the second eye stimulus, stimuli presentation subsystem 123 tests the first eye again to confirm that the first eye stimulus was the first detected stimulus. In another example, the stimuli presentation subsystem 123 retests the first eye if the second eye detects a stimulus with the same display characteristic level as that detected by the first eye, confirming whether the two eyes detected the same stimulus level or whether the second eye incidentally observed the first eye stimulus at block 506 (rather than the first eye). If the system determines to retest the eye that first detected the corresponding stimulus, the testing process can proceed in a similar manner to that described previously: the stimulus detected second can be turned off or reduced to a display characteristic level below the level at which it was observed, while the stimulus detected first is presented again at the level at which it was previously determined to be detected. If the first detected stimulus is not detected at the level, the stimuli presentation subsystem 123 sequentially increases the display characteristic level of the stimulus until feedback information indicates it has been detected. Once detected, feedback collection subsystem 124 replaces the stored value of the display characteristic level to the new level at which the user detected the stimulus.

In some embodiments, feedback collection subsystem 124 may continually store eye-related characteristic information during one or more steps of process 500. For example, throughout the visual test or retest, feedback collection subsystem 124 may store eye-related characteristic information. Eye-related characteristic information may include an eye movement, a gaze direction, a distance in which an eye's gaze traveled in the gaze direction, a pupil size change, a user-specific input, or other information obtained during the visual test or retest. Feedback collection subsystem 124 may store such eye-related characteristic information in second database 132 for later retrieval.

At block 522, the system 100 generates ocular anomaly information based on feedback information. For example, feedback collection subsystem 124 may use the stored measurements of the respective display characteristic levels of the stimuli detected by the first and second eyes to generate ocular anomaly information. Depending on the location of the stimuli and the levels at which the user detected them, the feedback collection subsystem 124 determines characteristics of the user's vision such as light sensitivity, distortions, or other aberrations related to one or more eyes of the user. The system 100 can determine one or more defective visual field portions of a visual field of a user (e.g., an automatic determination based on feedback related to the stimuli displayed to the user or other feedback). As an example, a defective visual field portion may be one of the visual field portions of the user's visual field that fails to satisfy one or more vision criteria (e.g., whether or an extent to which the user senses one or more stimuli, an extent of light sensitivity, distortion, or other aberration, or other criteria). In some embodiments, a defective visual field portion may be a portion of the user's visual field which matches a visual field defect pattern, such as regions of reduced vision sensitivity, regions of higher or lower optical aberrations, regions of reduced brightness, or other defective visual field portions.

In some embodiments, prediction model subsystem 125 may train or configure one or more prediction models to facilitate one or more embodiments described herein. In some embodiments, such models may be used to determine or otherwise generate ocular anomaly information. For instance, the prediction models may use feedback information, eye-characteristic information, or other information to generate ocular anomaly information for one or more eyes of a user. As an example, such models may be trained or configured to perform the foregoing functions by respectively mutually mapping input data and output data in nonlinear relationships based on learning (e.g., deep learning). Additionally, one or more pre-trained prediction models may be stored in first database 131. For example, first database 131 may store a plurality of pre-trained prediction learning models configured to generate predictions related to entity sets that are related to a first entity.

In some embodiments, the prediction models may include one or more neural networks or other machine learning models. As an example, neural networks may be based on a large collection of neural units (or artificial neurons). Neural networks may loosely mimic the manner in which a biological brain works (e.g., via large clusters of biological neurons connected by axons). Each neural unit of a neural network may be connected with many other neural units of the neural network. Such connections can be enforcing or inhibitory in their effect on the activation state of connected neural units. In some embodiments, each individual neural unit may have a summation function which combines the values of all its inputs together. In some embodiments, each connection (or the neural unit itself) may have a threshold function such that the signal must surpass the threshold before it propagates to other neural units. These neural network systems may be self-learning and trained, rather than explicitly programmed, and can perform significantly better in certain areas of problem solving, as compared to traditional computer programs. In some embodiments, neural networks may include multiple layers (e.g., where a signal path traverses from front layers to back layers). In some embodiments, back propagation techniques may be utilized by the neural networks, where forward stimulation is used to reset weights on the "front" neural units. In some embodiments, stimulation and inhibition for neural networks may be more free-flowing, with connections interacting in a more chaotic and complex fashion.

Figure 6:
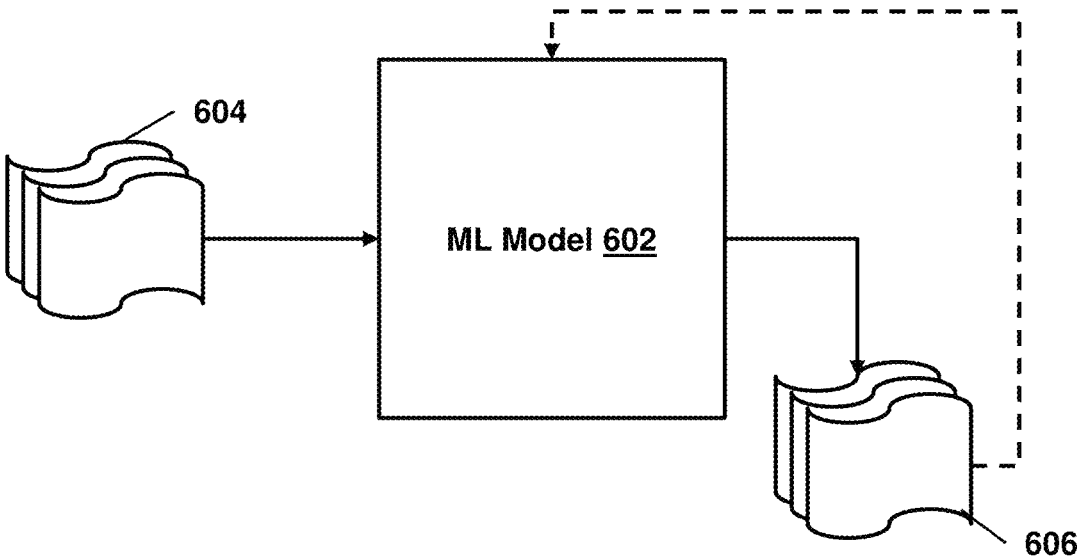
FIG. 6 shows a prediction model configured to generate ocular anomaly information, in accordance with one or more embodiments.

As an example, with respect to FIG. 6, machine learning model 602 may take inputs 604 and provide outputs 606. In one use case, outputs 606 may be fed back to machine learning model 602 as input to train machine learning model 602 (e.g., alone or in conjunction with user indications of the accuracy of outputs 606, labels associated with the inputs, or with other reference feedback information). In another use case, machine learning model 602 may update its configurations (e.g., weights, biases, or other parameters) based on its assessment of its prediction (e.g., outputs 606) and reference feedback information (e.g., user indication of accuracy, reference labels, or other information). In another use case, where machine learning model 602 is a neural network, connection weights may be adjusted to reconcile differences between the neural network's prediction and the reference feedback. In a further use case, one or more neurons (or nodes) of the neural network may require that their respective errors are sent backward through the neural network to them to facilitate the update process (e.g., backpropagation of error). Updates to the connection weights may, for example, be reflective of the magnitude of error propagated backward after a forward pass has been completed. In this way, for example, the machine learning model 602 may be trained to generate better predictions.

As an example, where the prediction models include a neural network, the neural network may include one or more input layers, hidden layers, and output layers. The input and output layers may respectively include one or more nodes, and the hidden layers may each include a plurality of nodes. When an overall neural network includes multiple portions trained for different objectives, there may or may not be input layers or output layers between the different portions. The neural network may also include different input layers to receive various input data. Also, in differing examples, data may input to the input layer in various forms, and in various dimensional forms, input to respective nodes of the input layer of the neural network. In the neural network, nodes of layers other than the output layer are connected to nodes of a subsequent layer through links for transmitting output signals or information from the current layer to the subsequent layer, for example. The number of the links may correspond to the number of the nodes included in the subsequent layer. For example, in adjacent fully connected layers, each node of a current layer may have a respective link to each node of the subsequent layer, noting that in some examples, such full connections may later be pruned or minimized during training or optimization. In a recurrent structure, a node of a layer may be again input to the same node or layer at a subsequent time, while in a bi-directional structure, forward and backward connections may be provided. The links are also referred to as connections or connection weights, as referring to the hardware implemented connections or the corresponding "connection weights" provided by those connections of the neural network. During training and implementation such connections and connection weights may be selectively implemented, removed, and varied to generate or obtain a resultant neural network that is thereby trained and that may be correspondingly implemented for the trained objective, such as for any of the above example recognition objectives.

In some embodiments, machine learning model 602 may be trained based on information stored in databases 130. For example, machine learning model 602 may be trained based on feedback information, eye-related characteristic information, or a combination thereof stored in second database 132 to generate predictions related to ocular anomalies present in one or more eyes of a user. For instance, machine learning model 602 may take feedback information, such as one or more measurements obtained during a visual test as input 604, and generate ocular anomaly information as outputs 606 that are related to (or otherwise associated with) the feedback information. In some embodiments, machine learning model 602 may take eye-related characteristic information, such as eye movement information of one or more eyes as input 604 and generate ocular anomaly information as outputs 606 that are related to (or otherwise associated with) the eye-related characteristic information. In some embodiments, the outputs 606 may be fed back into machine learning model 602 to update one or more configurations (e.g., weights, biases, or other parameters) based on its assessment of its prediction (e.g., outputs 606) and reference feedback information (e.g., user indication of accuracy, reference labels, or other information).

As an example, referring back to FIG. 1, in some embodiments, prediction model subsystem 125 may provide training data to a prediction model to train a prediction model. For instance, in some embodiments, prediction model subsystem 125 may obtain a prediction model (e.g., a machine learning model) from first database 131. In such a case, prediction model subsystem 125 may train the selected prediction model based on feedback information, eye-related characteristic information, or a combination thereof stored in second database 132 to generate predictions related to ocular anomalies present in one or more eyes of a user. Once the prediction model is trained, prediction model subsystem 125 may use the prediction model to detect the presence of an ocular anomaly. For example, in some embodiments, prediction model subsystem 125 may provide eye-tracking data for an eye, other feedback information, or a visual field map of the eye to the prediction model trained to detect one or more ocular anomalies associated with the eye (or one or more pretrained prediction models). The prediction model may perform operations to determine an anomaly boundary of an ocular anomaly, such as the shape of a defective area (e.g., a blind spot or other visual defect) in the peripheral region of an eye. Some embodiments may then use the predicted anomaly boundary to determine a future field location to test. For example, prediction model subsystem 125 determines whether the anomaly boundary overlaps with a stimuli boundary of a first display region and present a subsequent stimulus on a neighboring region of the first display region. Some embodiments may then perform an additional measurement to update the anomaly boundary of the ocular anomaly based on additional feedback information collected after the presentation of the second stimulus.

The concurrent visual testing process described with respect to FIG. 5 can improve the speed of the visual test. For example, by presenting at least some of the stimuli to the left eye and right eye at the same time, the system reduces the number of times it presents a stimulus and waits for feedback from the user to indicate whether the user detected the stimulus. Accordingly, the visual testing system described in implementations herein may consume fewer computational, time, or other resources related to such vision testing.

Figure 7:
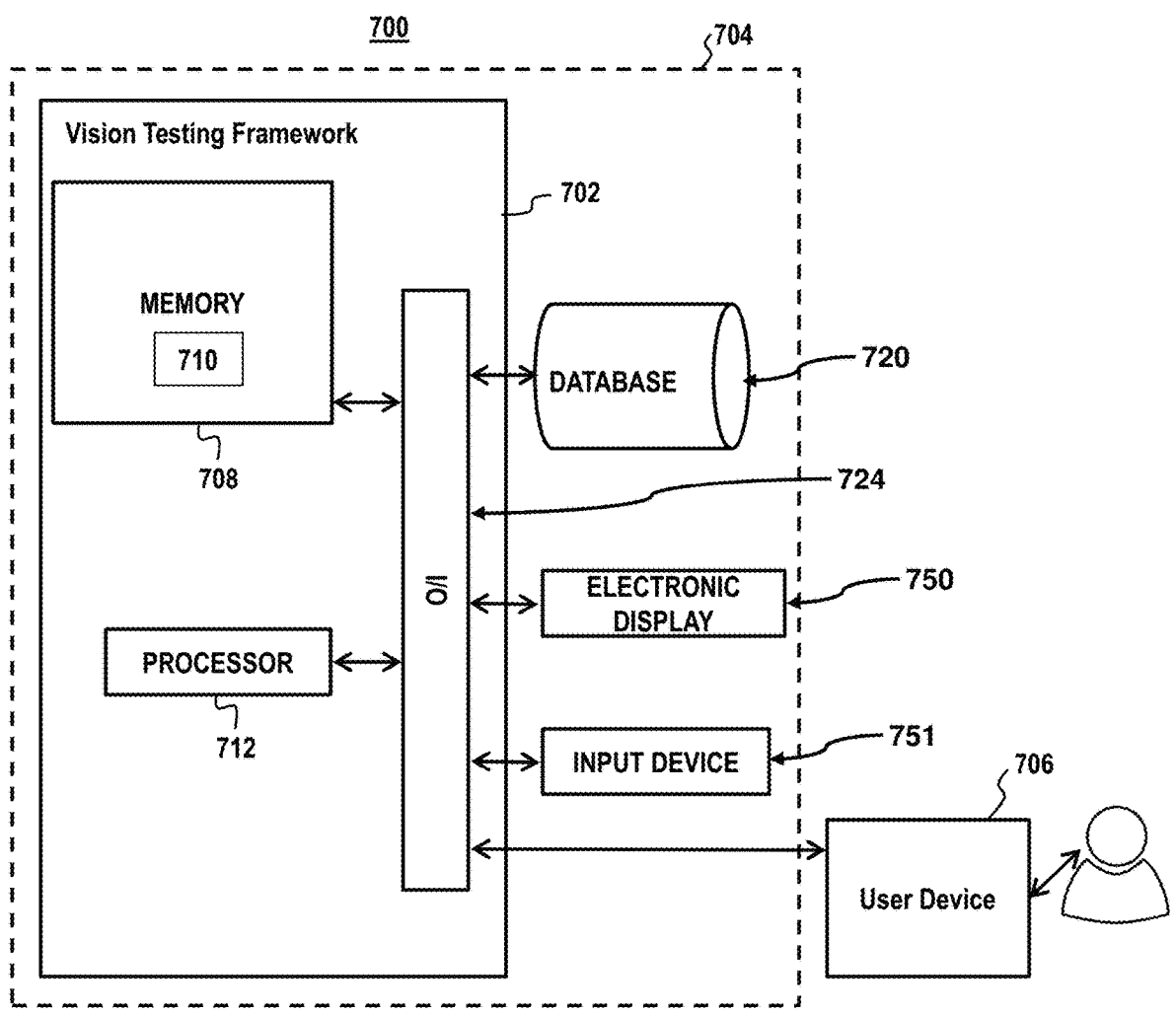
FIG. 7 shows a system with a testing framework implemented on a computer device and a user device, in accordance with one or more embodiments.

Aspects of the process 500 can be implemented by a vision system 700, an embodiment of which is illustrated in FIG. 7. In some embodiments, with respect to FIG. 7, system 100 may include a vision system 700, which includes a vision testing framework 702. The vision testing framework 702 may be implemented on an image processing device 704 and a wearable device 706 for placing on a subject. The image processing device 704 may be contained entirely in an external image processing device or other computer, while in other examples all or part of the image processing device 704 may be implemented within the wearable device 706.

The image processing device 704 may include a memory 708 storing instructions 710 that, when executed by the processor 712, for executing the testing and/or visioning modes described herein, may include instructions for collecting feedback information from the wearable device 706. In some embodiments, the wearable device 706 may capture real-time visual field image data as raw data, processed data, or pre-processed data. In some embodiments, a wearable device display of the wearable device 706 may be positioned in front of an eye and may present stimuli, such as characters, images, or other objects, where the eye's response may be used to generate or update a visual field map for the eye.

The wearable device 706 may be communicatively connected to the image processing device 704 through a wired or wireless link. The link may be through a Universal Serial Bus (USB), IEEE 1394 (Firewire), Ethernet, or other wired communication protocol device. The wireless connection can be through any suitable wireless communication protocol, such as Wi-Fi, NFC, iBeacon, Bluetooth, Bluetooth low energy, etc.

In various embodiments, the image processing device 704 may have a controller operatively connected to a database 720 via a link connected to an input/output (I/O) circuit 724. Additional databases may be linked to the controller in a known manner. The controller may include a program memory, the processor 712 (may be called a microcontroller or a microprocessor), a random-access memory (RAM), and the I/O circuit 724, all of which may be interconnected via an address/data bus. It should be appreciated that although only one microprocessor is described, the controller may include multiple microprocessors. Similarly, the memory of the controller may include multiple RAMs and multiple program memories. The RAM(s) and the program memories may be implemented as semiconductor memories, magnetically readable memories, and/or optically readable memories. The link may operatively connect the controller to the capture device, through the I/O circuit 724.

The program memory and/or the RAM may store various applications (i.e., machine readable instructions) for execution by the microprocessor. For example, an operating system may generally control the operation of the vision system 700 such as operations of the wearable device 706 and/or image processing device 704 and, in some embodiments, may provide a user interface to the device to implement the processes described herein. The program memory and/or the RAM may also store a variety of subroutines for accessing specific functions of the image processing device 704 described herein. By way of example, and without limitation, the subroutines may include, among other things: obtaining, from a spectacles device, high-resolution images of a visual field; enhancing and/or correcting the images; and providing the enhanced and/or corrected images for presentation to the subject by the wearable device 706.

In addition to the foregoing, the image processing device 704 may include other hardware resources. The device may also include or be connected to various types of I/O hardware such as an electronic display 750 and an input device 751, where the input device 751 may include devices such as keypads, keyboards, etc. In some embodiments, the electronic display 750 may be touch-sensitive and may cooperate with a software keyboard routine as one of the software routines to accept user input. It may be advantageous for the image processing device 704 to communicate with a broader network (not shown) through any of a number of known networking devices and techniques (e.g., through a computer network such as an intranet, the Internet, etc.). For example, the device may be connected to a database of ocular anomaly data.

The operations of each method presented in this disclosure are intended to be illustrative and non-limiting. It is contemplated that the operations or descriptions of FIG. 5 may be used with any other embodiment of this disclosure. In addition, the operations and descriptions described in relation to FIG. 5 may be done in alternative orders or in parallel to further the purposes of this disclosure. For example, each of these operations may be performed in any order, in parallel, or simultaneously to reduce lag or increase the speed of a computer system or method. In some embodiments, the methods may be accomplished with one or more additional operations not described, and/or without one or more of the operations discussed. Additionally, the order in which the processing operations of the methods are illustrated (and described below) is not intended to be limiting.

In some embodiments, the operations described in this disclosure may be implemented in one or more processing devices (e.g., a digital processor, an analog processor, a digital circuit designed to process information, an analog circuit designed to process information, a state machine, and/or other mechanisms for electronically processing information). The processing devices may include one or more devices executing some or all of the operations of the methods in response to instructions stored electronically on a non-transitory, machine-readable medium, such as an electronic storage medium. The processing devices may include one or more devices configured through hardware, firmware, and/or software to be specifically designed for execution of one or more of the operations of the methods. For example, it should be noted that any of the devices or equipment discussed in relation to FIG. 1, FIGS. 2A-2D, or FIG. 7 could be used to perform one or more of the operations in FIG. 5.

It should be noted that the features and limitations described in any one embodiment may be applied to any other embodiment herein, and a flowchart or examples relating to one embodiment may be combined with any other embodiment in a suitable manner, done in different orders, or done in parallel. In addition, the systems and methods described herein may be performed in real time. It should also be noted that the systems and/or methods described above may be applied to, or used in accordance with, other systems and/or methods.

In some embodiments, the various computer systems and subsystems illustrated in FIG. 1, FIGS. 2A-2D, or FIG. 7 may include one or more computing devices that are programmed to perform the functions described herein. The computing devices may include one or more electronic storages (e.g., the set of databases 130), one or more physical processors programmed with one or more computer program instructions, and/or other components. The computing devices may include communication lines or ports to enable the exchange of information with a set of networks (e.g., network 150) or other computing platforms via wired or wireless techniques. The network may include the Internet, a mobile phone network, a mobile voice or data network (e.g., a 5G or LTE network), a cable network, a public switched telephone network, or other types of communications networks or combinations of communications networks. The network 150 may include one or more communications paths, such as Ethernet, a satellite path, a fiber-optic path, a cable path, a path that supports Internet communications (e.g., IPTV), free-space connections (e.g., for broadcast or other wireless signals), Wi-Fi, Bluetooth, near field communication, or any other suitable wired or wireless communications path or combination of such paths. The computing devices may include additional communication paths linking a plurality of hardware, software, and/or firmware components operating together. For example, the computing devices may be implemented by a cloud of computing platforms operating together as the computing devices.

Each of these devices described in this disclosure may also include electronic storages. The electronic storages may include non-transitory storage media that electronically stores information. The storage media of the electronic storages may include one or both of (i) system storage that is provided integrally (e.g., substantially non-removable) with servers or client devices, or (ii) removable storage that is removably connectable to the servers or client devices via, for example, a port (e.g., a USB port, a firewire port, etc.) or a drive (e.g., a disk drive, etc.). The electronic storages may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. The electronic storages may include one or more virtual storage resources (e.g., cloud storage, a virtual private network, and/or other virtual storage resources). An electronic storage may store software algorithms, information determined by the processors, information obtained from servers, information obtained from client devices, or other information that enables the functionality as described herein.

The processors may be programmed to provide information processing capabilities in the computing devices. As such, the processors may include one or more of a digital processor, an analog processor, a digital circuit designed to process information, an analog circuit designed to process information, a state machine, and/or other mechanisms for electronically processing information. In some embodiments, the processors may include a plurality of processing units. These processing units may be physically located within the same device, or the processors may represent processing functionality of a plurality of devices operating in coordination. The processors may be programmed to execute computer program instructions to perform functions described herein of subsystems 123-125 or other subsystems. The processors may be programmed to execute computer program instructions by software; hardware; firmware; some combination of software, hardware, or firmware; and/or other mechanisms for configuring processing capabilities on the processors.

It should be appreciated that the description of the functionality provided by the different subsystems 123-125 described herein is for illustrative purposes, and is not intended to be limiting, as any of subsystems 123-125 may provide more or less functionality than is described. For example, one or more of subsystems 123-125 may be eliminated, and some or all of its functionality may be provided by other ones of subsystems 123-125. As another example, additional subsystems may be programmed to perform some or all of the functionality attributed herein to one of subsystems 123-125.

With respect to the components of computer devices described in this disclosure, each of these devices may receive content and data via input/output (hereinafter "I/O") paths. Each of these devices may also include processors and/or control circuitry to send and receive commands, requests, and other suitable data using the I/O paths. The control circuitry may comprise any suitable processing, storage, and/or input/output circuitry. Further, some or all of the computer devices described in this disclosure may include a user input interface and/or a user output interface (e.g., a display) for use in receiving and displaying data. In some embodiments, a display such as a touchscreen may also act as user input interfaces. It should be noted that in some embodiments, one or more devices described in this disclosure may have neither user input interfaces nor displays and may instead receive and display content using another device (e.g., a dedicated display device such as a computer screen and/or a dedicated input device such as a remote control, mouse, voice input, etc.). Additionally, one or more of the devices described in this disclosure may run an application (or another suitable program) that performs one or more operations described in this disclosure.

Although the present invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the scope of the appended claims. For example, it is to be understood that the present invention contemplates that, to the extent possible, one or more features of any embodiment may be combined with one or more features of any other embodiment.

As used throughout this application, the word "can" and "may" are used in a permissive sense (i.e., meaning having the potential to), rather than the mandatory sense (i.e., meaning must). The words "include," "including," "includes" and the like mean including, but not limited to. As used throughout this application, the singular forms "a," "an," and "the" include plural referents unless the context clearly indicates otherwise. Thus, for example, reference to "an element" or "a element" includes a combination of two or more elements, notwithstanding use of other terms and phrases for one or more elements, such as "one or more." The term "or" is non-exclusive (i.e., encompassing both "and" and "or"), unless the context clearly indicates otherwise. Terms describing conditional relationships (e.g., "in response to X, Y," "upon X, Y," "if X, Y," "when X, Y," and the like) encompass causal relationships in which the antecedent is a necessary causal condition, the antecedent is a sufficient causal condition, or the antecedent is a contributory causal condition of the consequent (e.g., "state X occurs upon condition Y obtaining" is generic to "X occurs solely upon Y" and "X occurs upon Y and Z"). Such conditional relationships are not limited to consequences that instantly follow the antecedent obtaining, as some consequences may be delayed, and in conditional statements, antecedents are connected to their consequents (e.g., the antecedent is relevant to the likelihood of the consequent occurring). Statements in which a plurality of attributes or functions are mapped to a plurality of objects (e.g., one or more processors performing steps/operations A, B, C, and D) encompass both all such attributes or functions being mapped to all such objects and subsets of the attributes or functions being mapped to subsets of the attributes or functions (e.g., both all processors each performing steps/operations A-D, and a case in which processor 1 performs step/operation A, processor 2 performs step/operation B and part of step/operation C, and processor 3 performs part of step/operation C and step/operation D), unless otherwise indicated. Further, unless otherwise indicated, statements that one value or action is "based on" another condition or value encompass both instances in which the condition or value is the sole factor and instances in which the condition or value is one factor among a plurality of factors.

Unless the context clearly indicates otherwise, statements that "each" instance of some collection have some property should not be read to exclude cases where some otherwise identical or similar members of a larger collection do not have the property (i.e., each does not necessarily mean each and every). Limitations as to sequence of recited steps should not be read into the claims unless explicitly specified (e.g., with explicit language like "after performing X, performing Y"), in contrast to statements that might be improperly argued to imply sequence limitations (e.g., "performing X on items, performing Y on the X'ed items") used for purposes of making claims more readable rather than specifying sequence. Statements referring to "at least Z of A, B, and C" and the like (e.g., "at least Z of A, B, or C") refer to at least Z of the listed categories (A, B, and C) and do not require at least Z units in each category. Unless the context clearly indicates otherwise, it is appreciated that throughout this specification, discussions utilizing terms such as "processing," "computing," "calculating," "determining" or the like refer to actions or processes of a specific apparatus, such as a special purpose computer or a similar special purpose electronic processing/computing device. Furthermore, unless indicated otherwise, updating an item may include generating the item or modifying an existing time. Thus, updating a record may include generating a record or modifying the value of an already-generated value.

The present techniques will be better understood with reference to the following enumerated embodiments:

1. A method comprising: simultaneously presenting, via a user device, a first eye stimulus for a first eye of a user of the user device (e.g., on a first display/display portion for the first eye) and a second eye stimulus for a second eye of the user (e.g., on a second display/display portion for the second eye), the first eye stimulus and the second eye stimulus each being associated with a display characteristic level; sequentially increasing the display characteristic level of the first eye stimulus and the second eye stimulus until feedback information indicates detection of at least one of the first eye stimulus or the second eye stimulus by the user; in response to the feedback information indicating detection of the first eye stimulus by the user, presenting the second eye stimulus at one or more sequentially increasing display characteristic levels (e.g., at least until the feedback information indicates detection of the second eye stimulus); and generating ocular anomaly information based on the feedback information.

2. The method of the preceding embodiment, wherein the first eye stimulus has a display characteristic level greater than a display characteristic level of the second eye stimulus.

3. The method of any of embodiments 1-2, wherein the feedback information comprises a signal obtained from one or more sensors.

4. The method of embodiment 3, wherein the one or more sensors comprise one or more eye-tracking sensors.

5. The method of any of embodiments 1-4, wherein the feedback information is obtained during a visual test of the user.

6. The method of any of embodiments 1-5, wherein the first eye stimulus is presented via a first display of the user device and the second eye stimulus is presented via a second display of the user device.

7. The method of any of embodiments 1-6, wherein the first eye stimulus is identified as being detected by the user based on a determined probability.

8. The method of any of embodiments 1-7, wherein the feedback information comprises an explicit input from the user to confirm detection of the first eye stimulus or the second eye stimulus.

9. The method of any of embodiments 1-8, wherein the display characteristic level comprises a contrast level, a brightness level, a sharpness level, or an opacity level.

10. The method of any of embodiments 1-9, wherein the first eye stimulus is presented at a first location on a first eye display and the second eye stimulus is presented at a second location on a second eye display that corresponds to the first location.

11. The method of embodiment 10, wherein the first location corresponds to the foveal region of the user's vision.

12. The method of embodiment 10, wherein the first location corresponds to a peripheral region of the user's vision.

13. The method of any of embodiments 1-9, wherein the first eye stimulus is presented at a first location on a first eye display, and the second eye stimulus is presented at a second location on a second eye display that does not correspond to the first location.

14. The method of embodiment 13, wherein the first location is one of a location corresponding to a peripheral region or a foveal region of the user's vision and the second location is a location corresponding to the other of the peripheral region or the foveal region of the user's vision.

15. The method of any of embodiments 1-14, wherein increasing the display characteristic level of the first eye stimulus and the display characteristic level of the second eye stimulus comprises increasing the display characteristic level of the first eye stimulus and the display characteristic level of the second eye stimulus at different times.

16. The method of any of embodiments 1-15, wherein presenting the second eye stimulus at the one or more sequentially increasing display characteristic levels comprises presenting the second eye stimulus without the first eye stimulus.

17. The method of any of embodiments 1-16, wherein presenting the second eye stimulus at the one or more sequentially increasing display characteristic levels comprises presenting the second eye stimulus while the first eye stimulus is presented at a display characteristic level below the display characteristic level at which the feedback information indicated detection of the first eye stimulus or the second eye stimulus.

18. The method of any of embodiments 1-17, wherein increasing the display characteristic level of the first eye stimulus and the second eye stimulus comprises increasing the display characteristic level by a same amount.

19. The method of any of embodiments 1-18, wherein the user device is at least one of a wearable device, a smartphone, a tablet, a computer, or other ocular exam equipment.

20. The method of any of the preceding embodiments, wherein the simultaneous presenting of the first and second eye stimulus occurs at an initial time, and wherein the sequential increasing of the display characteristic level of the first eye stimulus and the display characteristic level occur in parallel, and wherein during the parallel, sequential increasing of the display characteristic levels, the user detects a given stimulus of the first eye stimulus or the second eye stimulus at a first time, and wherein a display characteristic level is stored for the detected given stimulus at the first time.

21. The method of the preceding embodiment, further comprising: subsequent to the first time, continuing to present the other stimulus to which the user did not detect at one or more sequentially increasing display characteristic levels while the given detected stimulus is no longer presented to the user.

22. The method of any of embodiments 20-21, further comprising: in response to the feedback information indicating the user has detected the other stimulus at a second time, storing the display characteristic level for the other detected stimulus at the second time.

23. The method of any of embodiments 20-22, further comprising: identifying, as the given detected stimulus, the first eye stimulus or the second eye stimulus based on a determined probability that the first eye stimulus or the second eye stimulus was detected at the first time.

24. The method of the preceding embodiment, wherein the first eye stimulus is identified as the given detected stimulus based on a rule that assigns a greater probability of detection to the first eye stimulus than to the second eye stimulus.

25. The method of embodiment 23, further comprising: identifying a direction of eye movement based on data obtained from the one or more eye tracking sensors; and determining the probability that the first eye stimulus or the second eye stimulus was detected at the first time based on the identified direction of eye movement at the first time.

26. The method of any of embodiments 20-22, further comprising, in response to the stored measurement of the display characteristic levels of the first eye stimulus and the second eye stimulus being the same, retest the eye corresponding to the given detected stimulus by presenting the given detected stimulus at a third time.

27. A tangible, non-transitory, machine-readable medium storing instructions that, when executed by a data processing apparatus, cause the data processing apparatus to perform operations comprising those of any of embodiments 1-26.

28. A system comprising: one or more processors; and memory storing instructions that, when executed by the processors, cause the processors to effectuate operations comprising those of any of embodiments 1-26.

I claim:

1. A headset for ocular anomaly detection, comprising:
one or more eye tracking sensors;
first and second eye displays; and
one or more processors executing computer program instructions that, when executed, cause operations comprising:
obtaining, via the one or more eye tracking sensors, during a visual test, feedback information related to whether a user of the headset has detected a presented stimulus;
simultaneously presenting, at an initial time during the visual test, a first eye stimulus and a second eye stimulus at a corresponding location of the first eye display and the corresponding location of the second eye display, respectively, the first eye stimulus presented at the initial time having a contrast that is greater than a contrast of the second eye stimulus presented at the initial time;
sequentially increasing, in parallel, the contrast of the first eye stimulus and the contrast of the second eye stimulus until the feedback information indicates that the user has detected at least one of the first eye stimulus or the second eye stimulus, the contrast of the first eye stimulus continuing to be greater than the contrast of the second eye stimulus throughout the visual test when the first and second eye stimuli are both presented simultaneously to the user;
in response to the feedback information indicating that an eye of the user has detected a given stimulus of the first eye stimulus or the second eye stimulus at a first time, storing a measurement of the contrast of the given detected stimulus at the first time;
continuing to present the other stimulus of the first eye stimulus or second eye stimulus at one or more sequentially increasing contrasts at the corresponding location of the respective display for the other stimulus while the given detected stimulus is no longer presented at the corresponding location of the respective display for the given detected stimulus;
in response to the feedback information indicating that the user has detected the other stimulus at a second time, storing a measurement of the contrast of the other detected stimulus at the second time; and
generating ocular anomaly information based on the stored measurements.

2. The headset of claim 1, wherein sequentially increasing the contrast of the first eye stimulus and the contrast of the second eye stimulus in parallel comprises simultaneously increasing the contrast of the first eye stimulus and the contrast of the second eye stimulus by a same contrast amount.

3. The headset of claim 1, wherein sequentially increasing the contrast of the first eye stimulus and the contrast of the second eye stimulus in parallel comprises increasing the contrast of the first eye stimulus and the contrast of the second eye stimulus by a same contrast amount, but at different times, before further increasing the contrast of either eye.

4. The headset of claim 1, wherein the instructions further cause operations comprising: identifying, as the given detected stimulus, the first eye stimulus or the second eye stimulus based on a determined probability that the first eye stimulus or the second eye stimulus was detected at the first time.

5. A method comprising:

obtaining, via one or more sensors, during a visual test, feedback information related to whether a user of a user device has detected a presented stimulus;

while maintaining a greater contrast for a first eye stimulus than a second eye stimulus that are presented via the user device, sequentially increasing contrasts of the first eye stimulus and the second eye stimulus at least until the feedback information indicates detection of at least one of the first eye stimulus or the second eye stimulus by the user;

in response to the feedback information indicating detection of the first eye stimulus by the user, continuing to present the second eye stimulus at sequentially increasing contrast until the feedback information indicates detection of the second eye stimulus by the user; and generating ocular anomaly information based on the feedback information.

6. The method of claim 5, wherein sequentially increasing the contrast of the first eye stimulus and the contrast of the second eye stimulus comprises increasing the contrast of the first eye stimulus and the contrast of the second eye stimulus by a same contrast amount, before further increasing the contrast of either eye.

7. The method of claim 5, wherein the first eye stimulus and the second eye stimulus are displayed on a first display and a second display, respectively, at locations that correspond to a foveal region of the user's vision.

8. The method of claim 5, wherein the first eye stimulus and the second eye stimulus are displayed on a first display and a second display, respectively, at locations that correspond to a peripheral region of the user's vision.

9. The method of claim 5, wherein one of the first eye stimulus and the second eye stimulus is displayed on a first display portion at a location that corresponds to a foveal region of the user's vision, and wherein the other of the first eye stimulus and second eye stimulus is displayed on a second display portion at a location that corresponds to a peripheral region of the user's vision.

10. The method of claim 5, wherein increasing the contrast of the first eye stimulus and the contrast of the second eye stimulus comprises simultaneously increasing the contrast of the first eye stimulus and the contrast of the second eye stimulus.

11. The method of claim 5, further comprising:

identifying the first eye stimulus as being detected by the user further based on a determined probability.

12. One or more non-transitory computer-readable media storing executable instructions that, when executed by one or more processors, cause operations to:

while maintaining a greater display characteristic level for a first eye stimulus for a first eye of a user than a second eye stimulus for a second eye of the user that are presented via a user device, sequentially increasing display characteristic levels of the first eye stimulus and the second eye stimulus at least until feedback information indicates detection of at least one of the first eye stimulus or the second eye stimulus by the user;

in response to the feedback information indicating detection of the first eye stimulus by the user, continuing to present the second eye stimulus at one or more sequentially increasing display characteristic levels at least until the feedback information indicates detection of the second eye stimulus by the user; and generating ocular anomaly information based on the feedback information.

13. The non-transitory computer-readable media of claim 12, wherein the feedback information comprises a signal obtained from one or more eye tracking sensors.

14. The non-transitory computer-readable media of claim 12, wherein the feedback information comprises an explicit input from the user to confirm detection of the first eye stimulus or the second eye stimulus.

15. The non-transitory computer-readable media of claim 12, wherein the display characteristic levels comprise a contrast level, a brightness level, a sharpness level, or an opacity level.

16. The non-transitory computer-readable media of claim 12, wherein the first eye stimulus is presented at a first location on a first eye display and the second eye stimulus is presented at a second location on a second eye display that corresponds to the first location.

17. The non-transitory computer-readable media of claim 12, wherein the first eye stimulus is presented at a first location on a first eye display, and the second eye stimulus is presented at a second location on a second eye display that does not correspond to the first location.

18. The non-transitory computer-readable media of claim 12, wherein presenting the second eye stimulus at the one or more sequentially increasing display characteristic levels comprises presenting the second eye stimulus without the first eye stimulus.

19. The non-transitory computer-readable media of claim 12, wherein presenting the second eye stimulus at the one or more sequentially increasing display characteristic levels comprises presenting the second eye stimulus while the first eye stimulus is presented at a display characteristic level below the display characteristic level at which the feedback information indicated detection of the first eye stimulus or the second eye stimulus.

20. The non-transitory computer-readable media of claim 12, wherein sequentially increasing the display characteristic level of the first eye stimulus and the display characteristic level of the second eye stimulus comprises increasing the display characteristic level of the first eye stimulus and the display characteristic level of the second eye stimulus by a same amount before further increasing the display characteristic level of either eye.

* * * * *